United States Patent
Inamoto et al.

(10) Patent No.: US 8,377,352 B2
(45) Date of Patent: Feb. 19, 2013

(54) MEDICAL CATHETER TUBES AND PROCESS FOR PRODUCTION THEREOF

(75) Inventors: Satoshi Inamoto, Settsu (JP); Fumihiko Nakao, Settsu (JP); Mitsuharu Korogi, Settsu (JP); Tsuyoshi Mihayashi, Settsu (JP)

(73) Assignee: Kaneka Corporation, Osaka-shi (JP)

( * ) Notice: Subject to any disclaimer, the term of this patent is extended or adjusted under 35 U.S.C. 154(b) by 58 days.

(21) Appl. No.: 13/064,493

(22) Filed: Mar. 29, 2011

(65) Prior Publication Data
US 2011/0180955 A1   Jul. 28, 2011

Related U.S. Application Data

(62) Division of application No. 12/089,708, filed on Apr. 9, 2008, now abandoned.

(30) Foreign Application Priority Data

Oct. 17, 2005   (JP) .................................. 2005-302099
Jan. 18, 2006   (JP) .................................. 2006-010472

(51) Int. Cl.
*B29C 47/00*   (2006.01)
(52) U.S. Cl. ....................................... 264/127; 264/109
(58) Field of Classification Search ................. None
See application file for complete search history.

(56) References Cited

U.S. PATENT DOCUMENTS

| | | | |
|---|---|---|---|
| 2,685,707 A | 8/1954 | Llewellyn | |
| 4,743,480 A | 5/1988 | Campbell et al. | 428/36 |
| 5,505,887 A * | 4/1996 | Zdrahala et al. | 264/127 |
| 5,965,074 A * | 10/1999 | Aubertin et al. | 264/112 |
| 6,305,428 B1 | 10/2001 | Nakamura et al. | 139/126 |
| 6,627,277 B1 * | 9/2003 | Uchida et al. | 428/35.7 |
| 6,870,020 B2 * | 3/2005 | Aten et al. | 526/247 |
| 7,740,781 B2 * | 6/2010 | Levy et al. | 264/171.14 |
| 2003/0082323 A1 * | 5/2003 | Venditti et al. | 428/36.9 |
| 2004/0144441 A1 | 7/2004 | Connor et al. | 138/141 |
| 2004/0213936 A1 | 10/2004 | Yoshimoto et al. | 428/36.91 |
| 2005/0064122 A1 | 3/2005 | Oyama et al. | 428/36.9 |
| 2006/0147666 A1 | 7/2006 | Christel et al. | 428/36.92 |
| 2007/0071930 A1 | 3/2007 | Shelby et al. | 428/36.92 |
| 2011/0040373 A1 * | 2/2011 | Humphrey et al. | 623/1.49 |

FOREIGN PATENT DOCUMENTS

| | | |
|---|---|---|
| EP | 0 267 719 | 5/1988 |
| EP | 1 469 361 | 10/2004 |
| JP | 62-152467 | 7/1987 |
| JP | 64-060928 | 3/1989 |
| JP | 09-241412 | 9/1997 |
| JP | 2000-051365 | 2/2000 |
| JP | 2000-136280 | 5/2000 |
| JP | 2000-316977 | 11/2000 |
| JP | 2002-045428 | 2/2002 |
| JP | 2003-254324 | 9/2003 |
| JP | 2004-340364 | 12/2004 |
| WO | WO 2004/037099 | 5/2004 |
| WO | WO 2004/060210 | 7/2004 |

* cited by examiner

*Primary Examiner* — Mary F Theisen
(74) *Attorney, Agent, or Firm* — Kratz, Quintos & Hanson, LLP

(57) ABSTRACT

A medical catheter tube containing a tetrafluoroethylene polymer, which has a wall thickness of 0.1 mm or below and exhibits a tensile strength (S1) at 1.0 mm displacement of 5.0 N/mm or above; and a process for the production of medical catheter tubes, characterized by molding a composition both a tetrafluoroethylene polymer and a lubricant having high affinity for the polymer by paste extrusion. The invention provides thin-wall medical catheter tubes excellent in elongation resistance, kink resistance and internal cavity lubricity.

5 Claims, 1 Drawing Sheet

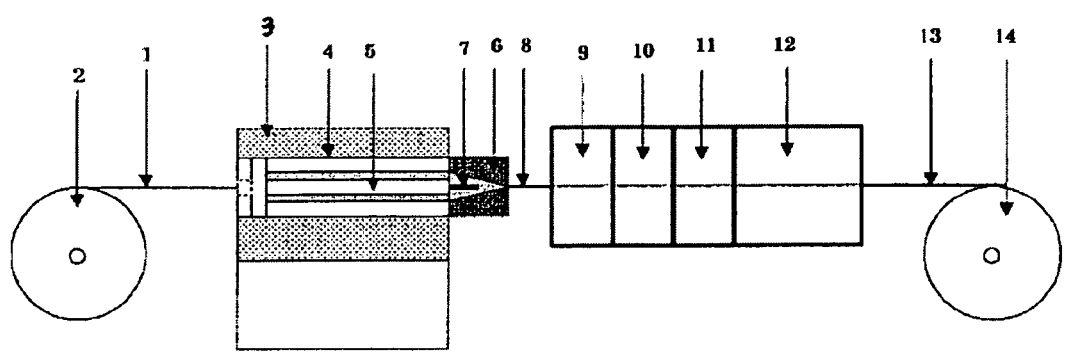

MEDICAL CATHETER TUBES AND PROCESS FOR PRODUCTION THEREOF

CROSS REFERENCE TO RELATED APPLICATIONS

This application is a division of U.S. patent application Ser. No. 12/089,708, filed Apr. 9, 2008 now abandoned, which application claims priority of Japanese Patent Application 2005-302099, filed Oct. 17, 2005 and Japanese Patent Application 2006-010472, filed Jan. 18, 2006, the entire contents of which are incorporated herein by reference.

TECHNICAL FIELD

The present invention relates to a catheter tube containing a tetrafluoroethylene polymer (hereinafter, referred to as "PTFE") favorably used in medical organizations such as hospitals and a production method of the catheter tube.

BACKGROUND ART

Less-invasive intravascular operation of inserting a catheter percutaneously into the blood vessel for treatment of vascular lesion is mainly practiced recently for reduction of physical and temporal loads applied on patients. Examples of such operation include a percutaneous blood vessel-forming operation of enlarging the stricture site of blood vessel or removing thrombus from thrombus-clotted blood vessel by applying negative pressure to the catheter, an intravascular operation called embolotherapy of injecting a thrombolic substance or a coil to lesions such as aneurysm, arteriovenous malfunction, and hemangioma often found in brain and other blood vessels.

The catheters for use in the percutaneous blood vessel-forming or intravascular operation demand, for example, the following properties.
(1) Favorable Operational Convenience and High Safety:

The catheter should be delivered rapidly and accurately to a lesion in the body without damage on vascular wall and others during insertion into the body. It is related to the efficiency of positional adjustment, for example, for reliable transmission of the surgeon's operation from the proximal region to the distal region during insertion or withdrawal of the catheter into or out of blood vessel and others.

Specifically, the positional adjustment efficiency is dependent on the resistance of catheter to elongation (stretch resistance), the efficiency of transmitting the torque from proximal region on the catheter, and the like.
(2) Preservation of Lumen Diameter and Reduction of Frictional Resistance of Lumen Surface:

These properties are related to the lumen lubricity and pressure resistance of catheter that are needed to inject a medicine such as contrast medium or thrombolic substance into the patient's internal lesion through the tube lumen, which is formed by a catheter internal layer resin, to remove intravascular substances such as thrombus and debris (foreign matter) smoothly out of the blood vessel for example by suction, or to deliver another treatment device such as guide wire less forcibly.

Specifically, it is needed to have a favorable guide wire-delivery efficiency of inserting and withdrawing the catheter smoothly along a previously-installed guide wire without damaging the internal wall of bent blood vessels. The catheter is desirably compatible with blood or organs. In addition, the catheter tube also demands favorable kink resistance prohibiting folding in the curved or bent area of blood-vessel when the distal end of catheter tube reaches a desired position and then the guide wire is removed and favorable distal-region flexibility keeping the shape favorable for the blood vessel without damaging it. It is necessary to reduce the external diameter of the tube for reduction of the frictional resistance with vascular wall and also to thin the internal layer of the catheter extremely (thinning) for prevention of decrease in medicinal flow rate and also in the flow resistance of intravascular substances and for increase of internal diameter.

To satisfy the requirements described above, this kind of catheter has, for example, a configuration having a multi-layer structure consisting of internal and external layers containing a resin and/or an elastomer and a reinforcement layer having a metal wire and/or a synthetic resin wire and also having a highly flexible distal region and a relatively rigid main body, wherein the rigidity of the catheter tube varies gradually from the distal region to the main body.

In particular, a fluoroethylene polymer (fluoroplastic), for example, is used as the material for the internal layer, for reduction of the frictional resistance on the lumen surface and thus for easier movement of the medicine or treatment device through the lumen. Specifically, tetrafluoroethylene polymers (PTFE's) superior in chemical resistance, low friction, and electric insulation efficiency are used widely.

As for the production method for catheter using PTFE, for example, Patent Documents 1, 2 and 3 disclose methods (dipping methods) of producing a catheter, by coating a core wire such as copper wire with a PTFE dispersion, forming an external resin layer thereon after sintering, and withdrawing the core wire.

However, the methods disclosed in the Patent Documents 1 to 3 gave catheters unsatisfactory in tensile strength because of absence of orientation and also in lumen lubricity during insertion or withdrawal of the guide wire because of separation of the PTFE particles. In addition, the catheters obtained by the method disclosed in the Patent Documents 1 to 3, which are not oriented, were unsatisfactory in kink resistance and positional adjustment efficiency (including stretch resistance and torque-transmitting efficiency). Further, it was necessary to repeat coating and sintering of a dispersion several times before obtaining a PTFE tube having a desired wall thickness, which caused problems of low productivity and local fluctuation in thickness by uneven coating.

In addition to the dipping methods disclosed in Patent Documents 1 to 3 above, extrusion molding methods are also used for producing catheters. The extrusion molding methods include melting extrusion molding and paste-extrusion molding. PTFE resins, which are very higher in melt viscosity, are molded not by melting extrusion molding, but normally by paste-extrusion molding.

For example, Patent Document 4 discloses a PTFE-based resin tube and a production method thereof, by extruding a PTFE-based resin, for example, by tube molding such as paste extrusion, sintering the extruded resin, and then, drawing and thus thinning the resin tube in the longitudinal direction by a drawing machine.

Patent Document 5 discloses an amorphous fluorine polymer superior in tensile strength allowing paste-extrusion molding, a PTFE composition containing a fluorine-containing chemical, and a production method thereof.

Patent Document 1: Japanese Unexamined Patent Publication No. 2000-316977
Patent Document 2: Japanese Unexamined Patent Publication No. 2000-51365
Patent Document 3: Japanese Unexamined Patent Publication No. 2002-45428

Patent Document 4: Japanese Unexamined Patent Publication No. 2004-340364

Patent Document 5: Japanese Unexamined Patent Publication No. 2000-136280

DISCLOSURE OF THE INVENTION

Problems to be Solved by the Invention

The method disclosed in Patent Document 4 above is not economical from the points of the cost for installing a drawing apparatus or a drawing process and also of the production cost. In addition, Patent Document 4 above only describes a method of enhancing the tensile strength of the PTFE-based tube for use in fuel transportation, for example as a brake hose, and the stretch resistance such as the tensile strength under microdisplacement, which is demanded for catheter, is not considered.

The method described in Patent Document 5 is nothing but a method aimed at reducing deformation during winding when a single layer sheet or a fibrous material obtained by paste extrusion is stored, and thus, thinning of the PTFE tube is not considered, because there is only a single layer. Further in the method, because thermal decomposition temperature of the amorphous fluorine polymer is low, there was a problem of air bubbling on the tube surface and also on the internal surface by the decomposition gas from the amorphous fluorine polymer during sintering, and also there was a concern about the biological compatibility because of the low-molecular-weight components generated.

As described above, the catheters disclosed in Patent Documents 1 to 3, which are prepared by dipping methods, are unsatisfactory in the kink resistance and the positional adjustment efficiency of the resulting catheters. In addition, as for the catheters of Patent Documents 4 and 5, which were prepared by paste-extrusion molding methods, the stretch resistance and thinning of the catheters were not considered. As a result, the catheters obtained in any one of prior arts do not satisfy all or part of the various requirements in the properties described above that are demanded, for example, when they are used in percutaneous blood vessel-forming operation or intravascular operation.

Under the circumstances above, an object of the present invention is to provide a medical catheter tube containing a tetrafluoroethylene polymer that satisfies the requirements in various properties for catheters and that is thin and superior in stretch resistance, kink resistance, and lumen lubricity stability, and a production method of the catheter tube.

Means to Solve the Problems

The present invention, which solved the problems above, has the following one or more aspects.

(1) An aspect of the present invention is a medical catheter tube containing a tetrafluoroethylene polymer, characterized by having a wall thickness of 0.1 mm or less and a tensile strength (S1) as determined at a displacement of 1.0 mm of 5.0 N/mm$^2$ or more.

(2) In a favorable embodiment, the melting point peak of the medical catheter tube is 320° C. or higher.

(3) Another aspect of the present invention is a medical catheter tube containing a tetrafluoroethylene polymer, characterized by having a wall thickness of 0.1 mm or less and a birefringence ($\Delta n1$) of $2.5 \times 10^{-3}$ or more.

(4) In a favorable embodiment, the medical catheter tube has a tensile strength (S1), as determined at a displacement of 1.0 mm, of 5.0 N/mm$^2$ or more.

(5) In a favorable embodiment, the tensile strength (S1) as determined at a displacement of 1.0 mm and the birefringence ($\Delta n1$) of the medical catheter tube satisfy the following relationship:

$$S1 \geq 170.0 \times \Delta n1 + 3.0.$$

(6) A yet another aspect of the present invention is a medical catheter tube improved in tensile strength, characterized in that, the medical catheter tube is a medical catheter tube containing a tetrafluoroethylene polymer; the polymer particles contained in the tetrafluoroethylene polymer are oriented in the axial direction of the catheter tube while the tetrafluoroethylene polymer is paste extrusion molded in the presence of a lubricant higher in compatibility with the tetrafluoroethylene polymer; and the distance among the polymer particles is shortened as the lubricant in the catheter tube is evaporated during drying.

(7) In a favorable embodiment, the tetrafluoroethylene polymer is oriented in the longitudinal direction.

(8) An yet another aspect of the present invention is a method of producing any one the medical catheter tubes described above, characterized by molding a composition containing the tetrafluoroethylene polymer and a lubricant higher in compatibility with the polymer by paste extrusion.

(9) In a favorable embodiment, the lubricant is a lubricant containing a fluorine-containing chemical.

(10) In a favorable embodiment, the lubricant is a lubricant containing a fluorine-containing chemical.

(11) In a favorable embodiment, the boiling point of the lubricant is 100° C. or higher.

(12) In a favorable embodiment, the difference (T1−T2) between the interfacial tension (T1) of the tetrafluoroethylene polymer and the interfacial tension (T2) of the lubricant is less than 3.6 dyne/cm.

(13) In a favorable embodiment, the method of producing the medical catheter tube further includes a drying step of heating at a temperature of the lubricant's boiling point or more.

(14) In a favorable embodiment, the production method further includes a sintering step of heating at a temperature of the tetrafluoroethylene polymer's melting point or more after the drying step.

(15) Another aspect of the present invention is a method of producing a medical catheter tube containing a tetrafluoroethylene polymer, characterized by including:

(a) an extrusion molding step of obtaining a molded tube by paste-extrusion molding the tetrafluoroethylene polymer in the presence of a lubricant higher in compatibility with the tetrafluoroethylene polymer for orientation of polymer particles contained in the tetrafluoroethylene polymer in the axial direction of the catheter tube; (b) a drying step of drying the molded tube at a temperature of the lubricant's boiling point or more, for removal of at least part of the lubricant contained in the molded tube and shortening of the distance among the particles contained in the tetrafluoroethylene polymer; and (c) a sintering step of sintering the molded tube after the drying step at a temperature of the tetrafluoroethylene polymer's melting point or more for fusion of the particles contained in the tetrafluoroethylene polymer with each other.

The aspects above, the other aspects and the advantageous effects of the invention will be described below more specifically in the following embodiments.

Advantageous Effects of the Invention

The present invention provides a thin medical catheter tube superior in stretch resistance, kink resistance, and lumen lubricity. In particular, the present invention provides a catheter tube resistant to deterioration in operational convenience, i.e., resistant to elongation by usage or operation during surgery and also to deterioration in lumen lubricity during device insertion, and a production method of the catheter tube.

BRIEF DESCRIPTION OF THE DRAWINGS

FIG. 1 is a schematic view showing the method of producing the catheter in an embodiment of the present invention.

EXPLANATION OF REFERENCES

| | |
|---|---|
| 1 | Metal core wire |
| 2 | Feed roll |
| 3 | Paste extruder |
| 4 | Extruder cylinder |
| 5 | Extruder mandrel |
| 6 | Die |
| 7 | Core pin |
| 8 | Molded tube |
| 9 | First drying oven |
| 10 | Second drying oven |
| 11 | Third drying oven |
| 12 | Sintering furnace |
| 13 | PTFE thin-film tube |
| 14 | Winding machine |

BEST MODE OF CARRYING OUT THE INVENTION

Hereinafter, the present invention will be described in detail with reference to embodiments.

1. Wall Thickness of Medical Catheter Tube

The "wall thickness" of the medical catheter tube according to the present invention is 0.10 mm or less, for example 0.005 to 0.10 mm, preferably 0.01 to 0.09 mm, and more preferably 0.02 to 0.08 mm. Because the wall thickness is low in the range above, it is possible to make the internal diameter relatively larger even when, for example, the entire thickness of the catheter tube is shortened, and thus, to avoid decrease in flow rate of medicine solution or in flow resistance of the intravascular substances. However, an excessively small wall thickness of the catheter tube may leads to deterioration in lubricity of the tube lumen surface, because of the frictional resistance during operation of the treatment device. Alternatively, excessively larger wall thickness is also unfavorable, because it makes the catheter less easily inserted into the blood vessel.

2. Melting Point Peak of Medical Catheter Tube

The melting point peak of the thin-layer medical catheter tube according to the present invention is not particularly limited, but for example 320° C. or higher, preferably 322° C. or higher, and more preferably 324° C. or higher. A melting point peak of lower than 320° C. is unfavorable because it may lead to easier deformation of the tube, making it difficult to adjust the position of the catheter tube during insertion of the treatment device. The upper limit of the melting point peak is preferably higher and thus, is for example 330° C. or lower, preferably 329° C. or lower, and more preferably 328° C. or lower, although it is not particularly limited.

3. Birefringence of Medical Catheter Tube

Hereinafter, the birefringence of the catheter tube will be described. The molecular orientation of a plastic molded product, which originates from flow and deformation during molding, gives rise to anisotropy in various properties. A typical example is the anisotropy in refractive index. The difference between two different refractive indices observed on an optically anisotropic article is defined as the birefringence. Thus, the birefringence is the difference between the refractive indices in a particular direction and the direction perpendicular thereto, i.e., an indicator of the magnitude of molecular orientation. Normally, larger birefringence, which is observed when the refractive index in a direction is larger than the refractive index in the direction perpendicular thereto, means that molecular orientation in one direction is larger than that in the direction perpendicular thereto.

Larger "birefringence ($\Delta n1$)" in the present invention, which is the difference between the refractive index of the medical catheter tube in the longitudinal direction and that in the circumferential direction perpendicular to the longitudinal direction, means improvement in stretch resistance, kink resistance, and lumen lubricity in the longitudinal direction. On the other hand, smaller birefringence unfavorably leads to deterioration in stretch resistance and elongation of the medical catheter tube, possibly causing a problem in positional adjustment efficiency for example during insertion of a treatment device such as catheter. The method for birefringence measurement will be described below.

The lower limit of the birefringence of the medical catheter tube according to the present invention is $2.5 \times 10^{-3}$ or more, preferably $2.7 \times 10^{-3}$ or more, and more preferably $3.0 \times 10^{-3}$ or more. The upper limit of the birefringence is not particularly limited if it is in the range above, but for example $5.0 \times 10^{-2}$ or less, more preferably, $4.0 \times 10^{-2}$ or less, and more preferably $3.0 \times 10^{-2}$ or less.

4. Tensile Strength of Medical Catheter Tube

The tensile strength (S1) (N/mm$^2$) at 1.0 mm displacement and the birefringence ($\Delta n1$) of the medical catheter tube according to the present invention satisfies the following Formula:

$$S1 \geq 170.0 \times \Delta n1 + 3.0,$$

preferably, $S1 \geq 200.0 \times \Delta n1 + 3.0$, and more preferably $S1 \geq 410.0 \times \Delta n1 + 3.0$.

When the following relationship is satisfied:

$$S1 < 170.0 \times \Delta n1 + 3.0$$

The PTFE particles therein are less oriented, often leading to elongation of the medical catheter tube or deterioration in lumen lubricity due to separation of the PTFE particles, consequently causing problems of difficulty in positional adjustment efficiency during insertion of the treatment device such as guide wire and also in insertion of the device.

The "tensile strength" of the medical catheter tube according to the present invention is not particularly limited, but the lower limit thereof at a displacement of 1.0 mm in the longitudinal direction is 5.0 N/mm$^2$ or more, preferably 7.0 N/mm$^2$ or more, and more preferably 10.0 N/mm$^2$ or more. The upper limit of the tensile strength is not particularly limited if it is in the range, but may be, for example, 150.0 N/mm$^2$ or less, more preferably 100.0 N/mm$^2$ or less, and more preferably 50.0 N/mm$^2$ or less. An excessively smaller tensile strength may unfavorably lead to elongation of the medical catheter tube, which in turn causes, for example, the problem of difficulty in positional adjustment efficiency during insertion of the treatment device such as guide wire.

5. Tetrafluoroethylene Polymer

The tetrafluoroethylene polymer particles contained in the "tetrafluoroethylene polymer" according to the present invention are preferably oriented as much as possible in the longitudinal direction of the medical catheter tube. The concept "polymer particles contained in the tetrafluoroethylene polymer are oriented in the axial direction orientation of the catheter tube by paste-extrusion molding" in the present invention includes, for example, a case where the orientation coefficient of the catheter tube in the longitudinal direction, as determined by wide-angle X-ray diffraction, is 0.2 or more (see e.g., Fluoroplastics Handbook (1990, Nikkankogyo Shimbun, Takaomi Satokawa Ed.). Orientation in the longitudinal direction leads to shortening of the distance between neighboring particles and thus, acceleration of fusion between the particles during sintering. Thus, paste extrusion leads to flow orientation of the tetrafluoroethylene polymer particles in the longitudinal direction, and thus, to enhance fusion of the particles and improvement in tensile strength of the tube obtained.

The tetrafluoroethylene polymer powders include, for example, those obtained by pulverization and those by emulsion polymerization. Use of a PTFE fine powder obtained by emulsion polymerization, which is easy to take fibrilation and is used commonly during paste-extrusion molding, is favorable in embodiments of the present invention.

6. Lubricant

The "lubricant" according to the present invention is not particularly limited, but, is preferably, for example, a lubricant that gives a paste with a fine powder that is processable by extrusion molding and that is favorably compatible with the tetrafluoroethylene polymer (including the tetrafluoroethylene polymer powder).

The "lubricant" is preferably a lubricant having a boiling point of 100° C. or higher, because such a lubricant is higher in compatibility with the tetrafluoroethylene polymer having relatively higher molecular weight. Favorably, a lubricant containing a fluorine-containing chemical (hereinafter, referred to as fluorine-based lubricant) and having a boiling point of 100° C. or higher may be used as the "lubricant".

The difference (T1−T2) between the interfacial tension (T1) of the tetrafluoroethylene polymer according to the present invention and the interfacial tension (T2) of the lubricant containing a fluorine-containing chemical is not particularly limited, but preferably less than 3.6 dyne/cm. Unfavorably, a difference in interfacial tension of 3.6 dyne/cm or more leads to deterioration in compatibility between the polymer and the lubricant and also to rapid increase in ram pressure during paste extrusion, prohibiting continuously paste-extrusion molding. The difference (T1−T2) is favorably as small as possible, but may be 0.1 dyne/cm or more, from the viewpoint of lubricant boiling point.

Examples of the fluorine-based lubricants include perfluorooctane (boiling point: 100° C.), perfluoro(2-butyltetrahydrofuran) (boiling point: 107° C.), perfluorotributylamine (boiling point: 180° C.), and the like.

A lubricant having a boiling point of lower than 100° C. is more volatile and unfavorable from the viewpoint of moldability during paste extrusion. Alternatively, lubricants having a boiling point of 220° C. or lower, preferably having a boiling point of 120 to 200° C., are particularly favorable, because it is possible to remove the lubricant reliably from the molded article by drying after extruding.

7. Composition

As for the ratios of the tetrafluoroethylene polymer and the fluorine containing chemical lubricant in the composition, the lubricant may be used in an amount in the range of 10 to 100 wt parts with respect to 100 wt parts of the tetrafluoroethylene polymer powder, but preferably 25 to 85 wt parts, particularly preferably 40 to 70 wt parts, from the viewpoint of extrusion molding efficiency.

The composition containing the tetrafluoroethylene polymer powder and the lubricant compatible with the tetrafluoroethylene may have additives such as X-Ray contrast medium powder, dispersion stabilizer, viscosity improver, surfactant and pH adjuster in the range that does not impair the favorable properties thereof. Examples of the materials for the X-Ray contrast medium powder include tungsten, gold, platinum, barium sulfate, bismuth oxide, hydroxy acid bismuth salts, bismuth subcarbonate, zirconium oxide, bismuth trioxide, tantalum, sodium iodide, silver-protein colloid, silver chloride-gelatin colloid, thorium oxide (IV) sol, iodine/pyrrolidone/sodium acetate, stainless steel powder, titanium powder, and the like.

8. Production Method for Catheter Tube

The production method for the medical catheter tube according to the present invention is not particularly limited, but use of a paste extrusion method is preferably, and any known paste extrusion method may be used (see e.g., Fluoroplastics Handbook (1990, Nikkankogyo Shimbun, Takaomi Satokawa Ed.)).

FIG. 1 is a schematic view showing the production method in an embodiment of the present invention. The production method has a paste-extrusion molding step (paste-extrusion molding), a drying step, and a sintering step. The production method according to the present invention includes other production methods suitably modified from the method in the above-mentioned embodiment within the scope of the present invention as defined in Claims.

The production system shown in FIG. 1 has a wire-feeding machine 2 carrying a wound metal core wire 1, a paste extruder 3, an extruder cylinder 4, an extruder mandrel 5, a die 6, a core pin 7, a molded tube 8, a first drying oven 9, a second drying oven 10, a third drying oven 11, a sintering furnace 12, a PTFE thin-film tube 13, and a winding machine 14.

The metal core wire 1, which is wound around the wire-feeding machine 2, has an external diameter almost identical with the internal diameter of the desired catheter described below. The material for the metal core wire 1 is preferably an annealed copper wire or a stainless steel wire plated with a metal such as silver or nickel.

Subsequently, a PTFE composition containing a lubricant above is extruded, coated, and molded on the metal core wire by the paste extruder 3, to give a molded tube 8. Then, the coat-molded tube 8 is fed into the drying ovens 9 to 11 for drying treatment and into the sintering furnace 12 for sintering treatment sequentially, to give a PTFE thin-film tube 13, while the traveling speed is adjusted by the winding machine 14. The extruder cylinder 4, the extruder mandrel 5, the die 6, or the core pin 7 may be adjusted properly, for production of a PTFE tube having desired external and internal diameters.

The drying treatment in the production method according to the present invention is not particularly limited, but the lubricant is removed from the molded tube 8, for example, while it is dried at a temperature of the lubricant's boiling point or more in the drying ovens 9 to 11. Common heat drying ovens and hot air-circulation drying ovens are used favorably as the drying ovens 9 to 11. The drying treatment at a temperature of lower than the lubricant's boiling point may unfavorably lead to cracking or generation of pores by bumping of the lubricant remaining in the tube during sintering described below.

The sintering treatment in the production method according to the present invention is not particularly limited, but, for example, treatment at a temperature of the PTFE's melting point or higher in the sintering furnace 12 is favorable for mutual fusion of the PTFE particles.

The melting point of PTFE is 320 to 330° C. Accordingly, the lower limit of the sintering treatment is 340° C. or higher, preferably 370° C. or higher, more preferably 400° C. or higher, while the upper limit of the sintering temperature is 650° C. or lower, preferably 620° C. or lower, and more preferably 590° C. or lower.

A common heat-sintering furnace or a hot air-circulation sintering furnace may be used as the sintering furnace 12. Sintering at a temperature of lower than the PTFE's melting point unfavorably leads to insufficient sintering and cracking of the resulting catheter tube due to fibrillation caused by the stress during winding.

As described above, the production method in the present embodiment is characterized by including the steps of (i) paste-extrusion molding a PTFE composition containing a tetrafluoroethylene polymer (PTFE) and a lubricant higher in compatibility therewith, while allowing orientation of the polymer particles as much as possible in the longitudinal direction, ("orientation of tetrafluoroethylene polymer in the longitudinal direction"), (uniformization of particle orientation by using a high-compatibility lubricant, corresponding to "paste-extrusion molding of a composition containing a tetrafluoroethylene polymer and a lubricant higher in compatibility with the polymer"),
(ii) narrowing the distance among the polymer particles by evaporating the lubricant by drying (densification of particles by removal of lubricant), and
(iii) fusing the densely dispersed particles with each other by melting part of the PTFE particles by sintering (fusion of particles). Because of the fusion of the particles with each other, the catheter tube obtained in the present embodiment has, for example, excellent tensile strength.

As described above, the improvement in tensile strength due to orientation of polymer particles in the longitudinal direction, by using a lubricant higher in compatibility with PTFE, shortening the distance among the particles by vaporization of the lubricant, and improving the efficiency of fusion among the particles is based on the finding of the inventors of the present application. The Patent Document 5 described above discloses a PTFE composition containing a fluorine polymer. However, the fluorine polymer described in the document is non-crystalline and functions as an adhesive to the PTFE polymer particles when used, and thus, does not have the advantage mainly concerning orientation and fusion of particles of the "lubricant containing a fluorine-containing chemical" described in the embodiment of the present invention.

9. Evaluation Methods

The evaluation values in the present description are determined in the following manners.

(Moldability)

The tube external diameter was monitored online during paste extrusion, by using a laser microdiameter manufactured by Takikawa Engineering Co., Ltd. When an external diameter of the average tube external diameter+0.03 mm or more is observed, the moldability was rated x, while, when it is lower than 0.03 mm, the moldability was rated O.

(Stretch Resistance Test: Tensile Strength)

A stretch resistance test was performed by using Strograph EII manufactured by Toyo Seiki Seisaku-sho, Ltd. and a load cell 50N at a chuck distance of 50 mm and a chuck speed of 100 mm/min. The stretch resistance load used was the stress ($N/mm^2$) of the tube when stretched by 1.0 mm in the longitudinal direction.

(Catheter Tube Wall Thickness)

The external diameter of the tube and the diameter of the core wire were determined, by using a laser microdiameter manufactured by Takikawa Engineering Co. The wall thickness was calculated according to the following Formula.

(Wall thickness/mm)=(tube external diameter/mm−core wire diameter/mm)/2

(Melting Point Peak)

The melting point peak was determined by using a differential scanning calorimeter manufactured by Shimadzu Corporation under the condition of a programmed heating rate of 10° C./minute, and under nitrogen gas air flow (30 mL/minute). The melting point peak was the melting endothermic peak observed.

(Lubricant Boiling Point)

The boiling point was determined by using a gas chromatograph (GC System HP6890 series) manufactured by Hewlett Packard.

(Birefringence)

The birefringence measurement method will be described below. The birefringence is represented by the following Formula.

$$\Delta n = Re/t$$

wherein, $\Delta n$ represents birefringence; Re, retardation (unit: for example mm (millimeter)); and t, sample thickness (unit: for example mm (millimeter)). The retardation and the sample thickness are practically measurable, and the retardation is the phase difference of a polarized light generated by the difference in refractive index of the sample during transmission thereof through the sample held between two polarization plates. The retardation was determined by using a simple retardation analyzer manufactured by Oji Scientific Instruments Co., Ltd. The thickness used was the wall thickness of the catheter tube described above.

(Powder Interfacial Tension)

The interfacial tension (T1) of the tetrafluoroethylene polymer powder was determined from Polymer Handbook Ver. 4, V/33 (18.6 dyne/cm). The interfacial tension (T2) of the lubricant containing a fluorine-containing chemical was determined by using a DUNOUY'S Precision Tension Meter manufactured by Yoshida Seisakusho Co., Ltd. under the condition of a temperature of 23° C. and a relative humidity of 50%.

(Kink-Resistance Test)

A kink-resistance test was performed by using an E-Z Test available from Shimadzu Corporation and a load cell 1N, at a chuck distance of 120 mm and a chuck speed of 50 mm/min. The kink length is calculated as follows:

(Kink length/mm)=(Initial loop length/mm)−(Kink tensile length/mm)

The kink period was determined by visual observation. Shorter kink length indicates superior kink resistance.

(Lumen Lubricity Test)

Three loops with a diameter φ of 16.5 mm were formed at the terminal of a tube; pure water was injected into the tube, and the guide wire was moved reciprocally 50 times at a stroke of 25 mm and a test speed of 500 mm/min in Strograph EII manufactured by Toyo Seiki Seisaku-sho, Ltd. The stress after the guide wire was reciprocated for one time, and the stress after the guide wire was reciprocated for 50 times were used as the indicator of the lumen lubricity. When there is smaller difference between the initial and post-50-reciprocation stresses, the lumen is superior in lubricity.

EXAMPLES

Hereinafter, the present invention will be described specifically with reference to Examples and Comparative Examples, but it should be understood that the present invention is not limited to these Examples. In the following Examples and Comparative Examples, catheter tubes were prepared in the apparatus shown in FIG. 1, unless specified otherwise.

Example 1

100 wt parts of a PTFE fine powder A (product name: Polyflon PTFE F-207, produced by Daikin Industries, Ltd) and 56 wt parts of a lubricant A (product name: Kosei Sol FC-1, available from Kosei Trading Co. Ltd., boiling point: 120° C., interfacial tension: 15.5 dyne/cm) were placed in a glass bottle; the mixture was left still in a constant temperature oven at 50° C. for 24 hours for aging, and then, cooled to room temperature and mixed by shaking. After mixing, the mixture was compressed at a pressure of 1.0 MPa for 5 minutes in a preforming cylinder of 18 mm$\phi$ in width for preparation of a preform. The primary preform obtained was placed in the cylinder of an extrusion molding machine and preformed additionally at a pressure of 28 MPa for 30 seconds with the head closed, for removal of air bubbles in the preform. The internal diameter of the extruder cylinder 4 in the paste extruder 3 was 18 mm; the external diameter of the extruder mandrel 5 was 12 mm; a die 6 having an internal diameter of 0.60 mm and a core pin 7 having an external diameter of 0.56 mm were used; and the cylinder and die temperatures were set respectively to 30° C.

Subsequently, the molded tube 8 extruded from the paste extruder 3 at a ram velocity of 1.5 mm/minute was fed through a first drying oven 9 set to 240° C., a second drying oven 10 set to 300° C., a third drying oven 11 set to 420° C., and a sintering furnace 12 set to 540° C., and wound at a velocity of 3.0 m/minute by the winding machine 14, to give a PTFE thin-film tube 13 having an external diameter of 0.58 mm and an internal diameter of 0.52 mm.

The moldability during paste extrusion was rated O. The tensile strength of the PTFE thin-film tube obtained, as determined at a displacement of 1.0 mm, was 7.0 N/mm$^2$. The kink length determined was 43 mm. The stress after one reciprocation in the lumen lubricity test was 0.48N, while that after 50 reciprocations was 0.47N.

Example 2

A PTFE thin-film tube was prepared in a similar manner to Example 1, except that 56 wt parts of a lubricant B (product name: Fluorinert FC-40, available from Sumitomo 3 M Ltd., boiling point: 155° C., surface tension: 16.0 dyne/cm) was added. The moldability during paste extrusion was rated O. The tensile strength of the PTFE thin-film tube obtained, as determined at a displacement of 1.0 mm, was 7.6 N/mm$^2$. The kink length determined was 42 mm. The stress after one reciprocation in the lumen lubricity test was 0.45N, while that after 50 reciprocations was 0.47N.

Example 3

A PTFE thin-film tube was prepared in a similar manner to Example 1, except that 56 wt parts of a lubricant C (product name: Fluorinert FC-43, manufactured by Sumitomo 3 M Ltd., boiling point: 174° C., surface tension: 16.0 dyne/cm) was added. The moldability during paste extrusion was rated O. The tensile strength of the PTFE thin-film tube obtained, as determined at a displacement of 1.0 mm, was 6.4 N/mm$^2$. The kink length determined was 45 mm. The stress after one reciprocation in the lumen lubricity test was 0.43N, while that after 50 reciprocations was 0.45N.

Example 4

A PTFE thin-film tube was prepared in a similar manner to Example 1, except that 100 wt parts of a PTFE fine powder B (product name: Polyflon PTFE F-201, produced by Daikin Industries) was added. The moldability during paste extrusion was rated O. The tensile strength of the PTFE thin-film tube obtained, as determined at a displacement of 1.0 mm, was 7.8 N/mm$^2$. The kink length determined was 42 mm. The stress after one reciprocation in the lumen lubricity test was 0.50N, while that after 50 reciprocations was 0.48N.

Example 5

A PTFE thin-film tube was prepared in a similar manner to Example 2, except that a core pin having an external diameter of 0.46 mm and a die having an internal diameter of 0.50 mm were used. The moldability during paste extrusion was rated O. The tensile strength of the PTFE thin-film tube obtained, as determined at a displacement of 1.0 mm, was 9.7 N/mm$^2$. The kink length determined was 34 mm. The stress after one reciprocation in the lumen lubricity test was 0.60N, while that after 50 reciprocations was 0.58N.

Comparative Example 1

A PTFE dispersion (product name: PTFE AD-1, manufactured by Asahi Glass Co., Ltd.) was coated and sintered repeatedly on a silver-plated annealed copper wire having a diameter of 0.52 mm, to give a PTFE thin-film tube having an external diameter of 0.58 mm and an internal diameter of 0.52 mm. The tensile strength of the PTFE thin-film tube obtained, as determined at a displacement of 1.0 mm, was 4.3 N/mm$^2$. The kink length determined was 56 mm. The stress after one reciprocation in the lumen lubricity test was 0.48N, while that after 50 reciprocations was 0.73N.

Comparative Example 2

A PTFE thin-film tube was prepared in a similar manner to Example 1, except that 56 wt parts of a lubricant D (product name: Fluorinert FC-77, manufactured by Sumitomo 3M Ltd., boiling point: 97° C., surface tension: 15.0 dyne/cm) was added. However, the tube could not be extruded uniformly, and the moldability of paste extrusion was rated x, and the silver-plated annealed copper wire was broken during molding.

Comparative Example 3

A PTFE thin-film tube was prepared in a similar manner to Example 1, except that 56 wt parts of a lubricant E (product name: Isopar M, manufactured by Exxon Mobil Corporation, boiling point: 198° C., interfacial tension) was added. However, PTFE particles were fibrillated, prohibiting uniformly extrusion; the moldability of paste extrusion was rated x; and the silver-plated annealed copper wire was broken during molding.

The results above are summarized in Table 1.

The results in Examples and Comparative Examples of Table 1 show that it is possible to reduce deterioration in moldability, kink resistance, stretch resistance and lumen lubricity, by adding a lubricant containing a fluorine-containing chemical to a tetrafluoroethylene-based polymer powder and paste-extruding the mixture. In particular, orientation of PTFE particles by paste extrusion has a significant influence on the stretch resistance. It is because the catheter becomes more resistant to external force and improved in kink resistance, stretch resistance, and lumen lubricity by orientation and fusion of the PTFE particles.

TABLE 1

| | unit | Exmaple1 | Exmaple2 | Exmaple3 | Exmaple4 | Exmaple5 | Comparative Example1 | Comparative Example2 | Comparative Example3 |
|---|---|---|---|---|---|---|---|---|---|
| PTFE | — | A | A | A | B | A | Dispersion | A | A |
| Total amount | wt parts | 100 | 100 | 100 | 100 | 100 | 100 | 100 | 100 |
| (parts) | | | | | | | | | |
| Lubricant | — | A | B | C | A | A | — | D | E |
| Total amount | wt parts | 56 | 56 | 56 | 56 | 56 | — | 56 | 23 |
| (parts) | | | | | | | | | |
| Die internal diameter | mm | 0.60 | 0.60 | 0.60 | 0.60 | 0.50 | — | 0.60 | 0.60 |
| Core pin external diameter | mm | 0.56 | 0.56 | 0.56 | 0.56 | 0.46 | — | 0.56 | 0.56 |
| PTFE external diameter | mm | 0.58 | 0.58 | 0.58 | 0.58 | 0.48 | 0.58 | — | — |
| PTFE internal diameter | mm | 0.52 | 0.52 | 0.52 | 0.52 | 0.42 | 0.52 | — | — |
| PTFE wall thickness | mm | 0.03 | 0.03 | 0.03 | 0.03 | 0.03 | 0.03 | — | — |
| Moldability | ○ or × | ○ | ○ | ○ | ○ | ○ | — | × | × |
| Tensile strength (at 1-mm displacement) | N/mm2 | 7.0 | 7.6 | 6.4 | 7.8 | 9.7 | 4.3 | — | — |
| Kink length | mm | 43 | 42 | 45 | 42 | 34 | 56 | — | — |
| Guide wire stress (one reciprocation) | N | 0.48 | 0.45 | 0.43 | 0.50 | 0.60 | 0.48 | — | — |
| Guide wire stress (50 reciprocations) | N | 0.47 | 0.47 | 0.45 | 0.48 | 0.58 | 0.73 | — | — |

Catheter tubes were prepared in the above apparatus shown in FIG. 1 also in the following Examples and Comparative Examples similarly to those above, unless specified otherwise.

Example 6

100 wt parts of a PTFE fine powder A (product name: Polyflon PTFE F-207, produced by Daikin Industries, Ltd) and 56 wt parts of lubricant A (product name: Fluorinert FC-40, manufactured by Sumitomo 3M Ltd., boiling point: 155° C., surface tension: 16.0 dyne/cm) were placed in a glass bottle; and the mixture was left still in a constant temperature oven at 50° C. for 24 hours for aging, and then, cooled to room temperature and mixed by shaking. The lubricant A was highly compatible with the tetrafluoroethylene polymer, contained a perfluorotetrahydrofuran-based fluorine-containing chemical, and had a boiling point of 150° C. or higher.

After mixing, the mixture was compressed at a pressure of 1.0 MPa for five minutes in a preforming cylinder of 18 mmφ, for preparation of a preform. The primary preform obtained was placed in the cylinder of an extrusion molding machine and preformed additionally at a pressure of 28 MPa for 30 seconds with the head closed. The internal diameter of the extruder cylinder 4 in the paste extruder 3 was 18 mm; the external diameter of the extruder mandrel 5 was 12 mm; a die 6 having an internal diameter of 0.60 mm and a core pin 7 having an external diameter of 0.56 mm were used; and the cylinder and die temperatures were set respectively to 30° C.

Subsequently, the molded tube 8 extruded from the paste extruder 3 at a ram velocity of 1.5 mm/minute was fed through a first drying oven 9 set to 240° C., a second drying oven 10 set to 300° C., a third drying oven 11 set to 420° C., and a sintering furnace 12 set to 540° C., and wound at a velocity of 3.0 m/minute by the winding machine, to give a PTFE thin-film tube 13 having an external diameter of 0.58 mm and an internal diameter of 0.52 mm.

The birefringence of the PTFE thin-film tube obtained was $1.3 \times 10^{-2}$. The tensile strength of the PTFE thin-film tube obtained, as determined at a displacement of 1.0 mm, was 7.6 N/mm$^2$. The kink length determined was 42 mm. The stress after one reciprocation in the lumen lubricity test was 0.45N, while that after 50 reciprocations was 0.47N.

Example 7

A PTFE thin-film tube was prepared in a similar manner to Example 6, except that a core pin having an external diameter of 0.56 mm and a die having an internal diameter 0.61 mm were used. The birefringence of the PTFE thin-film tube obtained was $6.4 \times 10^{-3}$. The tensile strength of the PTFE thin-film tube obtained, as determined at a displacement of 1.0 mm, was 7.0 N/mm$^2$. The kink length determined was 43 mm. The stress after one reciprocation in the lumen lubricity test was 0.48N, while that after 50 reciprocations was 0.47N.

Example 8

A PTFE thin-film tube was prepared in a similar manner to Example 6, except that a core pin having an external diameter of 0.56 mm and a die having an internal diameter 0.58 mm were used. The birefringence of the PTFE thin-film tube obtained was $8.9 \times 10^{-3}$. The tensile strength, as determined at a displacement of 1.0 mm, was 6.4 N/mm$^2$. The kink length determined was 45 mm. The stress after one reciprocation in the lumen lubricity test was 0.43N, while that after 50 reciprocations was 0.45N.

Example 9

A PTFE thin-film tube was prepared in a similar manner to Example 6, except that 100 wt parts of a PTFE fine powder B (product name: Fluon PTFE CD090, manufactured by Asahi Glass Co., Ltd.) was added. The birefringence of the PTFE thin-film tube obtained was $1.3 \times 10^{-2}$. The tensile strength, as determined at a displacement of 1.0 mm, was 5.9 N/mm$^2$. The kink length determined was 46 mm. The stress after one reciprocation in the lumen lubricity test was 0.50N, while that after 50 reciprocations was 0.48N.

Example 10

A PTFE thin-film tube was prepared in a similar manner to Example 6, except that 100 wt parts of a PTFE fine powder C (product name: Teflon PTFE 640-J, manufactured by Du Pont-Mitsui Fluorochemicals Co., Ltd.) was added. The birefringence of the PTFE thin-film tube obtained was $1.2 \times 10^{-2}$. The tensile strength of the PTFE thin-film tube obtained, as determined at a displacement of 1.0 mm, was 7.0 N/mm$^2$. The kink length determined was 42 mm. The stress after one reciprocation in the lumen lubricity test was 0.49N, while that after 50 reciprocations was 0.47N.

Example 11

A PTFE thin-film tube was prepared in a similar manner to Example 6, except that a core pin having an external diameter of 0.46 mm and a die having an internal diameter of 0.50 mm were used. The birefringence of the PTFE thin-film tube obtained was $1.2 \times 10^{-2}$. The tensile strength of the PTFE thin-film tube obtained, as determined at a displacement of 1.0 mm, was 9.7 N/mm$^2$. The kink length determined was 34 mm. The stress after one reciprocation in the lumen lubricity test was 0.60N, while that after 50 reciprocations was 0.58N.

Hereinafter, catheter tubes in Comparative Examples 4 to 8 were prepared for comparison with Examples 6 to 11. Comparative Examples 4, 7, and 8 were same respectively as Examples 6, 7, and 9, in PTFE external diameter, internal diameter, and wall thickness. Comparative Example 5 was the same as Example 11 in PTFE external shape, internal diameter, and thickness.

Comparative Examples are different, in that the PTFE was coated and sintered, from Examples 6 and 10, which employed a paste extrusion molding step and a drying-sintering step. In addition, no lubricant was used in Comparative Examples.

Comparative Example 4

A PTFE dispersion (product name: PTFE dispersion AD-1, manufactured by Asahi Glass Co., Ltd.) was coated and sintered repeatedly on a silver-plated annealed copper wire having a diameter of 0.52 mm, to give a PTFE thin-film tube having an external diameter of 0.58 mm and an internal diameter of 0.52 mm. The birefringence of the PTFE thin-film tube obtained was $2.0 \times 10^{-3}$. The tensile strength of the PTFE thin-film tube obtained, as determined at a displacement of 1.0 mm, was 4.3 N/mm$^2$. The kink length determined was 56 mm. The stress after one reciprocation in the lumen lubricity test was 0.48N, while that after 50 reciprocations was 0.73N.

Comparative Example 5

A PTFE thin-film tube was prepared in a similar manner to Comparative Example 4, except that the resin was coated and sintered on a silver-plated copper wire having a diameter of 0.42 mm, to give a PTFE thin-film tube having an external diameter of 0.48 mm and an internal diameter of 0.42 mm. The birefringence of the PTFE thin-film tube obtained was $2.1 \times 10^{-3}$. The tensile strength of the PTFE thin-film tube obtained, as determined at a displacement of 1.0 mm, was 4.1 N/mm$^2$. The kink length determined was 48 mm. The stress after one reciprocation in the lumen lubricity test was 0.61N, while that after 50 reciprocations was 0.84N.

Comparative Example 6

A PTFE thin-film tube was prepared in a similar manner to Comparative Example 4, to give a PTFE thin-film tube having an external diameter of 0.46 mm and an internal diameter of 0.42 mm. The birefringence of the PTFE thin-film tube obtained was $2.3 \times 10^{-3}$. The tensile strength of the PTFE thin-film tube obtained, as determined at a displacement of 1.0 mm, was 3.7 N/mm$^2$. The kink length determined was 62 mm. The stress after one reciprocation in the lumen lubricity test was 0.63N, while that after 50 reciprocations was 1.15N.

Comparative Example 7

A PTFE thin-film tube was prepared in a similar manner to Comparative Example 4, except that a PTFE dispersion E (product name: Teflon PTFE dispersion 30, manufactured by Du Pont-Mitsui Fluorochemicals Co., Ltd.) was used. The birefringence of the PTFE thin-film tube obtained was $2.2 \times 10^{-3}$. The tensile strength of the PTFE thin-film tube obtained, as determined at a displacement of 1.0 mm, was 4.1 N/mm$^2$. The kink length determined was 58 mm. The stress after one reciprocation in the lumen lubricity test was 0.52N, while that after 50 reciprocations was 0.80N.

Comparative Example 8

A PTFE thin-film tube was prepared in a similar manner to Comparative Example 4, except that a PTFE dispersion F (product name: Polyflon PTFE dispersion D-1E, manufactured by Daikin Industries Co. Ltd.) was used. The birefringence of the PTFE thin-film tube obtained was $2.2 \times 10^{-3}$. The tensile strength of the PTFE thin-film tube obtained, as determined at a displacement of 1.0 mm, was 4.0 N/mm$^2$. The kink length determined was 55 mm. The stress after one reciprocation in the lumen lubricity test was 0.50N, while that after 50 reciprocations was 0.77N.

The measurement results of the tubes obtained in Examples 6 to 11 and Comparative Examples 4 to 8 are summarized in Table 2.

(T2) of the lubricant is less than 3.6 dyne/cm., by paste extrusion, and drying by heating at a temperature of the lubricant boiling point or higher.

TABLE 2

| | unit | Exmaple6 | Exmaple7 | Exmaple8 | Exmaple9 | Exmaple 10 | Exmaple 11 | Comparative Example4 | Comparative Example5 | Comparative Example6 | Comparative Example7 | Comparative Example8 |
|---|---|---|---|---|---|---|---|---|---|---|---|---|
| PTFE | — | A | A | A | B | C | A | D | D | D | E | F |
| Total amount (parts) | wt parts | 100 | 100 | 100 | 100 | 100 | 100 | 100 | 100 | 100 | 100 | 100 |
| Lubricant | — | A | A | A | A | A | A | — | — | — | — | — |
| Total amount (parts) | wt parts | 56 | 56 | 56 | 56 | 56 | 56 | — | — | — | — | — |
| Die internal diameter | mm | 0.60 | 0.61 | 0.58 | 0.60 | 0.60 | 0.50 | — | — | — | — | — |
| Core pin external diameter | mm | 0.56 | 0.56 | 0.56 | 0.56 | 0.56 | 0.46 | — | — | — | — | — |
| PTFE external diameter | mm | 0.58 | 0.58 | 0.56 | 0.58 | 0.58 | 0.48 | 0.58 | 0.48 | 0.46 | 0.58 | 0.58 |
| PTFE internal diameter | mm | 0.52 | 0.52 | 0.52 | 0.52 | 0.52 | 0.42 | 0.52 | 0.42 | 0.42 | 0.52 | 0.52 |
| PTFE wall thickness | mm | 0.03 | 0.03 | 0.02 | 0.03 | 0.03 | 0.03 | 0.03 | 0.03 | 0.02 | 0.03 | 0.03 |
| Birefringence | — | $1.3 \times 10^{-2}$ * | $6.4 \times 10^{-3}$ * | $8.9 \times 10^{-3}$ * | $1.3 \times 10^{-2}$ * | $1.2 \times 10^{-2}$ * | $1.2 \times 10^{-2}$ * | $2.0 \times 10^{-3}$ * | $2.1 \times 10^{-3}$ * | $2.3 \times 10^{-3}$ * | $2.2 \times 10^{-3}$ * | $2.2 \times 10^{-3}$ * |
| Tensile strength (at 1-mm displacement) | N/mm² | 7.6 | 7.0 | 6.4 | 5.9 | 7.0 | 9.7 | 4.3 | 4.1 | 3.7 | 4.1 | 4.0 |
| Kink length | mm | 42 | 43 | 45 | 46 | 42 | 34 | 56 | 48 | 62 | 58 | 55 |
| Guide wire stress (one reciprocation) | N | 0.45 | 0.48 | 0.43 | 0.50 | 0.49 | 0.60 | 0.48 | 0.61 | 0.63 | 0.52 | 0.50 |
| Guide wire stress (50 reciprocations) | N | 0.47 | 0.47 | 0.45 | 0.48 | 0.47 | 0.58 | 0.73 | 0.84 | 1.15 | 0.80 | 0.77 |

The results of Examples and Comparative Examples in Table 2 show that a birefringence of $2.5 \times 10^{-3}$ or more leads to thinning of catheter wall (see, for example, "PTFE wall thickness" in Table 2), improvement in stretch resistance (see "tensile strength" in Table 1) and kink resistance (see "kink length" in Table 2), and resistance to deterioration in lumen lubricity (see "guide wire-stress (one) and (50)" in Table 2). Obviously, the catheter becomes more resistant to external force and improved in kink resistance, stretch resistance, and lumen lubricity, by orientation and fusion of the PTFE particles.

The invention claimed is:

1. A method of producing a medical catheter tube containing a tetrafluoroethylene polymer, the tube having:
   a wall thickness of less than 0.1 mm; and
   a tensile strength (S1) as determined at a displacement of 1.0 mm of 5.0 N/mm² or more;
   characterized by molding a composition containing the tetrafluoroethylene polymer and a lubricant, containing a fluorine-containing chemical, and having a boiling point of 100° C. or higher, and wherein the difference (T1–T2) between the interfacial tension (T1) of the tetrafluoroethylene polymer and the interfacial tension (T2) of the lubricant is less than 3.6 dyne/cm., by paste extrusion, and drying by heating at a temperature of the lubricant boiling point or higher.

2. The production method according to claim 1, wherein the tetrafluoroethylene polymer powder is a tetrafluoroethylene polymer powder prepared by an emulsion polymerization method.

3. A method of producing a medical catheter tube containing a tetrafluoroethylene polymer, the tube having:
   a wall thickness of less than 0.1 mm; and
   a tensile strength (S1) as determined at a displacement of 1.0 mm of 5.0 N/mm² or more;
   characterized by molding a composition containing the tetrafluoroethylene polymer and a lubricant, containing a fluorine-containing chemical, and having a boiling point of 100° C. or higher, and wherein the difference (T1–T2) between the interfacial tension (T1) of the tetrafluoroethylene polymer and the interfacial tension (T2) of the lubricant is less than 3.6 dyne/cm., by paste extrusion, and drying the molded tube at a temperature of the lubricant boiling point or higher, for removal of at least part of the lubricant contained in the molded tube and shortening of the distance among the particles contained in the tetrafluoroethylene polymer.

4. The production method according to claim 3, wherein the tetrafluoroethylene polymer powder is a tetrafluoroethylene polymer powder prepared by an emulsion polymerization method.

5. A method of producing a medical catheter tube containing a tetrafluoroethylene polymer, characterized by including:

(a) an extrusion molding step of obtaining a molded tube by paste-extrusion molding the tetrafluoroethylene polymer in the presence of a lubricant, and having a boiling point of 100° C. or higher, and wherein the difference (T1−T2) between the interfacial tension (T1) of the tetrafluoroethylene polymer and the interfacial tension (T2) of the lubricant is less than 3.6 dyne/cm., for orientation of polymer particles contained in the tetrafluoroethylene polymer in the axial direction of the catheter tube;

(b) a drying step of drying the molded tube at a temperature of the lubricant boiling point or higher, for removal of at least part of the lubricant contained in the molded tube and shortening of the distance among the particles contained in the tetrafluoroethylene polymer; and (c) a sintering step of sintering the molded tube after the drying step at a temperature of the tetrafluoroethylene polymer's melting point or more for fusion of the particles contained in the tetrafluoroethylene polymer with each other.

* * * * *